United States Patent
Levi et al.

(10) Patent No.: US 7,229,612 B2
(45) Date of Patent: *Jun. 12, 2007

(54) COMPOSITIONS FOR ELIMINATING HUMAN AND ANIMAL EXCREMENT SMELLS AND A METHOD FOR USE THEREIN

(75) Inventors: Shalom Levi, Beer Sheva (IL); Steve Daren, Nes Ziona (IL)

(73) Assignee: Damar Holdings S.A., Nassau (BS)

( * ) Notice: Subject to any disclaimer, the term of this patent is extended or adjusted under 35 U.S.C. 154(b) by 0 days.

This patent is subject to a terminal disclaimer.

(21) Appl. No.: 10/086,727

(22) Filed: Mar. 4, 2002

(65) Prior Publication Data

US 2002/0127195 A1 Sep. 12, 2002

Related U.S. Application Data

(63) Continuation of application No. 09/341,237, filed as application No. PCT/IL98/00016 on Jan. 14, 1998, now Pat. No. 6,413,506.

(30) Foreign Application Priority Data

Jan. 14, 1997 (IL) .................................. 120007

(51) Int. Cl.
*A01N 1/00* (2006.01)
*A01L 9/00* (2006.01)
*A01L 9/04* (2006.01)
*A01L 11/00* (2006.01)

(52) U.S. Cl. ............... 424/76.5; 424/75; 424/76.1; 424/76.2; 424/76.3; 424/76.4; 424/76.6

(58) Field of Classification Search .......... 424/65, 424/76.1, 78.03
See application file for complete search history.

(56) References Cited

U.S. PATENT DOCUMENTS

| 3,446,893 | A | * | 5/1969 | Hanford et al. ............ 424/76.3 |
| 3,878,303 | A | * | 4/1975 | Hashimoto .................... 426/56 |
| 3,954,964 | A | | 5/1976 | Kuderna, Jr. |
| 4,127,383 | A | | 11/1978 | Johnston et al. |
| 4,158,648 | A | * | 6/1979 | Meadus et al. ................ 524/45 |
| 4,405,354 | A | | 9/1983 | Thomas, II et al. |
| 4,839,089 | A | * | 6/1989 | Shimizu ................. 252/183.11 |
| 4,909,986 | A | * | 3/1990 | Kobayashi et al. ............ 422/4 |
| 5,004,600 | A | * | 4/1991 | Suzuki ...................... 424/76.3 |
| 5,039,481 | A | * | 8/1991 | Pacifici et al. ................. 422/4 |
| 5,429,650 | A | | 7/1995 | Hoffman et al. |
| 5,456,701 | A | | 10/1995 | Stout |
| 5,780,547 | A | * | 7/1998 | Saeki et al. .................... 525/61 |
| 5,882,638 | A | * | 3/1999 | Dodd et al. .................... 424/65 |
| 5,980,826 | A | * | 11/1999 | Barenberg et al. ............ 422/37 |
| 6,001,789 | A | | 12/1999 | Trinh et al. |
| 6,454,876 | B1 | * | 9/2002 | Ochomogo et al. ........... 134/42 |
| 2003/0049290 | A1 | * | 3/2003 | Jha et al. ..................... 424/401 |

FOREIGN PATENT DOCUMENTS

| EP | 0 354 281 | 2/1990 |
| WO | 81 02891 | 10/1981 |

* cited by examiner

*Primary Examiner*—Susan Tran
(74) *Attorney, Agent, or Firm*—Browdy and Neimark, PLLC

(57) ABSTRACT

The present invention related to compositions (deodorizing or not) for human and animal excrement, especially pest and livestock, comprised of acidic agents and water soluble polymers, wherein the acidic agents are base neutralizers for the ammonia and indolic amines in the excrement and the water soluble polymers are barrier forming agents for the vapor of the offensive odor producing compounds in the excrement and for slowing down the air oxidative and enzymatic nitrification of the excrement ammonia and organic nitrogen thus dispersing the attenuating nitrate concentrations in the environment. The present invention further relates to a method of applying said compositions to excrement. Said compositions may be applied to excrement in liquid form by mixing the liquid composition together with the excrement, or in the form of a spray, by spraying the composition directly onto the excrement.

17 Claims, No Drawings

COMPOSITIONS FOR ELIMINATING HUMAN AND ANIMAL EXCREMENT SMELLS AND A METHOD FOR USE THEREIN

The present application is a continuation of parent application Ser. No. 09/341,237 filed on Jul. 13, 1999, now U.S. Pat. No. 6,413,506 B1, the U.S. national phase of PCT/IL98/00016, filed Jan. 14, 1998.

FIELD OF THE INVENTION

The present invention relates generally to deodorant compositions for human and animal excrement and to a method for their use. The term "animal" as used in this specification refers especially to pets and livestock. More specifically the present invention relates to novel compositions, preferably aqueous compositions, comprised of acidic agents and water soluble polymers for applying on excrement, that are useful as deodorant compositions and for attenuating and dispersing nitrate concentrations in the environment and in the water reservoir, wherein the deodorizing of the excrement is based on acidification by organic acids and excrement coating by water soluble polymers which act as barriers for the offensive odor producing compounds of the excrement and form, upon drying, a film, turning the excrement into solid cakes easy to handle and with no perceptible odor.

BACKGROUND OF THE INVENTION

Owners of animals such as pets and livestock alike face problems caused by animal excrement; its foul odor and the need to eliminate it. Human excrement, such as in out houses in camp sites and army camps, pose the same problems. National and international regulations require that materials used for treating excrement, be non toxic and friendly to the environment, in particular that they do not contribute to adding nitrates or phosphates to the water reservoir. Additional requirements of commercial deodorizing compositions are low cost, simplicity of use in and outdoors and efficient deodorizing of excrement in liquid and solid forms.

The principle targets of most existing treatment methods for preventing offensive odors of animal excrement, are ammonia and indolic amines. The common method to prevent offensive odors and retard bacterial and enzymatic decomposition is converting these compounds to their much less volatile ammonium salts by various organic and inorganic acids or their salts, as described in numerous publications.

Although acidification prevents offensive odors originating from basic ammonia and amines, it intensifies the offensive odors due to the excrement's volatile organic acids such as acetic, propionic and butyric acids, due to the stabilization of their non ionized form. Furthermore, feces of low mobility do not come into contact with the deodorizing agents which are usually absorbed or sprayed on pet's litter and hence are only partially deodorized.

Therefore, there is a need for an inexpensive, effective and environment friendly composition which will include an impermeable barrier to excrement offensive odors in addition to safe deodorizing treatment of ammonia and indolic amines.

This impermeable barrier has an additional advantage of slowing down the air oxidative and enzymatic nitrification of the excrement ammonia and organic nitrogen, leading to dispersion and attenuation of nitrate concentrations in the environment.

Of the known deodorizing formulations for pet and livestock few, if any, are of practical use.

Use is made of cross-linked polymer gels, as water absorbing materials, in compositions for treatment of pet excrement, in several patents.

Japanese patents 5269164, 3290126 and 2238834 disclose polymer gels with high water absorbing capacity for absorbing animal excretions. These gels may previously be blended with deodorant agents.

Japanese patent 63185323 discloses absorbents for deodorizing pet excrement's. Polyvinyl alcohol is used as a binder in the production of pellets comprised of water absorbing inorganic polymers, like zeolites, and water soluble inorganic salts.

U.S. Pat. No. 5,039,481 describes $NH_3$ scavenging deodorant made of aliphatic polycarboxylic acids for treatment of livestock excrement.

Japanese patents 61119127 and 62153348 describe compositions for treating pet feces with a water insoluble coating to reduce odors and to enable feces to be removed by hand. These compositions, however, comprise toxic and ecologically unsafe volatile organic solvents such as acetone, methylene chloride, benzene, $CFCl_3$ and the expensive and toxic cyanoacrylate monomer.

The present invention describes novel deodorizing compositions comprising organic acids and water soluble polymers for excrement coating, which meet the above mentioned requirements. Furthermore, the present invention overcomes the two above mentioned major limitations of offensive odor due to stabilizing the non ionized form of excrement's volatile organic acids and low mobility feces not coming in full contact with the deodorizing composition, by incorporating water soluble barrier forming agents in the deodorant composition.

SUMMARY OF THE INVENTION

The present invention relates to deodorizing compositions for human and animal excrement, especially pets and livestock comprised of acidic agents and water soluble polymers, wherein the acidic agents are base neutralizers for the ammonia and indolic amines in the excrement and the water soluble polymers are film forming polymers of molecular weight higher than 15,000, forming a barrier for the vapor of the offensive odor producing compounds in the excrement. The present invention also relates to compositions (not necessarily deodorant compositions) comprised of acidic agents and water soluble polymers wherein the water soluble polymers are barrier forming agents useful for slowing down the air oxidative and enzymatic nitrification of the excrement ammonia and organic nitrogen thus dispersing and attenuating nitrate concentrations in the environment and in the water reservoir.

These composition are preferably an aqueous solution.

The present invention further relates to a method of applying said compositions to excrement. Said compositions may be applied to excrement in liquid form by mixing the liquid composition together with the excrement. This method is especially useful in treating livestock excrement. Said compositions may also be applied in form of a spray, by spraying the composition directly on to the excrement whereas, upon drying, the sprayed compositions form a thin film turning the excrement into solid cakes, easy to handle with no perceptible smell.

DETAILED DESCRIPTION OF THE INVENTION

The present invention relates to novel deodorizing compositions, preferably aqueous compositions, for human and animal excrement comprised of acidic agents and water soluble polymers, wherein the acidic agents are base neutralizers for the ammonia and indolic amines in the excrement and the water soluble polymers are barrier forming agents for the vapor of the offensive odor producing compounds in the excrement.

When applied on excrement these compositions form, upon drying, thin film barriers which greatly reduce the vapor pressure of the offensive odor producing compounds and the intensified offensive odors due to the acidification which stabilizes the non ionized form of the excrement's volatile organic acids such as acetic, propionic and butyric acids. In the case of solid feces this film also traps the ammonia and indolic amines that may escape contact with the deodorizing agent. These compositions form, upon drying, a thin film turning the excrement into solid cakes, easy to handle with no perceptible smell.

The acidic agents are preferably biodegradable organic acids or their soluble salts such as citric acid, glycolic acid, oxalic acid, polyacrylic acids, preferably in a concentration range of 1%-10%.

The water soluble polymers are preferably hydroxyethyl cellulose, polyethylene oxide, polyvinyl pyrrolidone, polyhydroxyethyl (meth)acrylate, polyvinyl alcohol, polyhydroxypropyl (meth)acrylate, poly(meth)acrylamide, which are biologically degradable, non toxic and ecologically safe, preferably in a concentration range of 0.1%-10%.

A fragrance, such as limonene, may be added to the compositions as natural fragrance.

The water soluble coating polymers (WSCP) used in this invention are biodegradable, non toxic and friendly to the environment and can be included in various deodorizing compositions.

The said invention will be further illustrated in detail by the following examples. These examples do not intend to limit the scope of the invention but to demonstrate and clarify it only.

In the following examples WSCP were added to compositions based on aqueous solutions of carboxylic acids or combinations of carboxylic acids or their soluble salts. These compositions were applied to different animal excrements.

EXAMPLE 1 solution 1: 5% (w/v) of polyvinyl alcohol (PVA) was obtained by dissolving 10 g of PVA (98% hydrolyzed, avg. M.W.=16,000) in 200 ml tap water (800 mho conductivity) at 70° C.

Composition 1.1 (2.5% PVA), a composition suitable for pets excrement was prepared from the following:

| | |
|---|---|
| solution 1 | 125 ml |
| water | 125 ml |
| citric acid | 12.5 g |
| monopotassium phosphate (MKP) | 12.5 g |
| limonene | 10 µl |

Composition 1.2 (1.5% PVA), a composition suitable for pets excrement and transported organic fertilizer, was prepared from the following:

| | |
|---|---|
| 1.5% PVA | 1000 ml |
| citric acid | 100 g |
| limonene | 20 µl |

Composition 1.1 was tested on cat litter in a family's home. 100 ml of composition 1.1 were sprayed on 2 kg of smelly cat litter, while slightly mixing the litter.

Uncovered feces were occasionally sprayed lightly and brushed aside.

A spraying bottle of 250 ml was used for two litter replacements in a three week period. During this time the excrement offensive smell was reduced significantly and replacement of the litter was needed only every 10 days as opposed to every 4 days, without treatment.

On completion of the experiment with composition 1.1, composition 1.2 was tested on the same cat litter with similar deodorizing efficiency results.

EXAMPLE 2

This example shows a composition suitable both for pet excrement and for spraying on transported organic fertilizer.

Composition 2

| | |
|---|---|
| 1.5% polyvinyl alcohol aqueous solution | 100 ml |
| Citric acid | 5 g |

The citric acid was dissolved in 7 ml water and the solution was slowly added to the polyvinyl alcohol solution while stirring.

40 ml of this solution were mixed with 200 ml of pig excrement collected from a cesspit adjacent to the sty. The pH of the excrement was reduced from 7 to 6. 200 ml of a control (excrement with no addition) were placed in an open beaker about 10 m apart from the excrement treated with composition 2 in the open air. After one hour in the sun a barrier film formed on the surface of the treated solution, preventing smell and protecting the underlying excrement from flies.

The polyvinyl alcohol-citric acid solution was tested on cat litter as described in example 1. Similar results were obtained and the replacement of the litter was not required for 10 days after the initial spray.

EXAMPLE 3

This example shows the effect of acidification in an aqueous media, such as oxidation ponds and livestock excrement pools.

Three samples of 20 liters of pig excrement, collected from a cesspit adjacent to the sty, were added to three 30 liter plastic tanks with a continuous air supply from air pumps.

The three samples were treated with the following:

| Composition 3.1 | |
|---|---|
| 450 ml | glycolic acid (70%) |
| 107 ml | ethylene glycol |
| 300 g | ferrous sulfate heptahydrate |

-continued

Composition 3.2

| 450 ml | glycolic acid (70%) |
| 300 g | ferrous sulfate heptahydrate |

Control (no addition)

The initial pH of the excrement was 7.1 (measured using a glass electrode). Addition of compositions 3.1 and 3.2 brought the pH to 4.5 and 4.6 respectively. The tanks were allowed to stand outdoors for six months. The water lost due to evaporation was periodically replaced to maintain a constant volume.

After six months the following observations were made:

|  | composition 3.1 | composition 3.2 | control |
| --- | --- | --- | --- |
| pH | 5.92 | 6.12 | 6.77 |
| color | brown | brown | black |
| smell | moderate | moderate | foul |
| fly maggots | none | none | several |

EXAMPLE 4

This example demonstrates the effect of the polymers as barrier forming agents. The water was decanted from the three tanks from example 2 (after 6 months) and the following solutions were added to about 5 liters of the residual sludge:
to 3.1 450 ml of a 10% polyvinyl pyrrolidone solution.
to 3.2 260 ml of an 8% polyethylene oxide solution.
the tanks were left in the sun for a week and the sludge dried out.

Sample 3.2 dried into a solid cake which could easily be handled and had no perceptible smell.

Sample 3.1 dried into a less strong cake and had a slight residual smell.

The control sample was dispersed and had a residual smell, but less than when it was mixed with water.

EXAMPLE 5

This example shows the effect of polyvinyl pyrrolidone as a barrier forming agent in cat litter.

A solution of 15 g of citric acid in 200 ml of water was added to 200 ml of a 2% solution of polyvinyl pyrrolidone with stirring. The pH of the solution formed by mixing was about 1.5. This mixture solution was sprayed on cat litter as described in example 1.

The excrement offensive smell was significantly reduced and replacement of the litter was needed only every 10 days as opposed to every 4 days, without treatment.

The invention claimed is:

1. Aqueous deodorizing composition for human and animal excrement, consisting essentially of
    tap water;
    an acid agent in an amount sufficient to neutralize ammonia and indolic amines in said excrement wherein the acid agent comprises at least one biodegradable carboxylic acid, whereby said composition is biodegradable; and
    at least 0.1% of at least one biologically degradable non-toxic and ecologically safe water soluble polymer, said polymer being present in an amount sufficient for forming, upon drying, a thin film vapor barrier on the excrement in a concentration range of 0.1% to 10% w/v;
    wherein the water soluble polymer is a barrier forming agent for the vapor of offensive odor producing compounds in the excrement and
    is selected from the group consisting of hydroxyethyl cellulose, polyethylene oxide, polyvinyl pyrrolidone, polyhydroxyethyl (meth) acrylate, polyvinyl alcohol, and polyhydroxypropyl methacrylate, and
    wherein the water soluble polymer has a molecular weight of higher than 15,000, and, when formed as a film over said excrement will eventually biodegrade.

2. Deodorizing composition according to claim 1 in film form on animal excrement of a pet or livestock.

3. Deodorizing composition according to claim 1, wherein the biodegradable carboxylic acid is selected from the group consisting of citric acid, glycolic acid, oxalic acid and polyacrylic acid.

4. Deodorizing composition according to claim 1, wherein the concentration range of the acid is 1%-10% w/v.

5. Deodorizing composition according to claim 1 further comprising a fragrance.

6. Deodorizing composition according to claim 1 wherein the fragrance is Limonene.

7. Deodorizing composition according to claim 6, wherein the Limonene is in a concentration range of 0.01-0.005% w/v.

8. Aqueous film-forming deodorizing composition for human and animal excrement consisting essentially of:
    tap water; p1 an acid agent comprising at least one biodegradable carboxylic acid, whereby said composition is biodegradable, in an amount sufficient to neutralize ammonia and indolic amines in said excrement; and
    at least 0.1% and up to about 10% of at least one biologically degradable, non-toxic, ecologically safe and water soluble polymer for forming, upon drying, a thin film vapor barrier on the excrement,
    wherein said water soluble film forming polymer is a polyacrylic acid and is capable of forming a barrier for the vapor of the offensive odor producing compounds in the excrement and wherein said water soluble film forming polymer has a molecular weight of higher than 15,000.

9. Aqueous deodorizing composition for human and animal excrement comprising:
    tap water;
    an acid agent comprising at least one biodegradable carboxylic acid, whereby said composition is biodegradable, in an amount sufficient to neutralize ammonia and indolic amines in said excrement; and
    at least 0.1% and up to about 10% of at least one biologically degradable non-toxic and ecologically safe water soluble polymer capable of forming, upon drying, a thin film vapor barrier on the excrement, for turning the excrement into a solid cake, and thereby comprising means for greatly reducing the vapor pressure of offensive odor producing compounds and facilitating easy handling of said deodorized excrement;
    wherein the biologically degradable and water soluble polymer is selected from the group consisting of hydroxyethyl cellulose, polyethylene oxide, polyvinyl pyrrolidone, polyhydroxyethyl (meth)acrylate, polyvinyl alcohol, and polyhydroxypropyl methacrylate, and wherein the biologically degradable water soluble polymer has a molecular weight of higher than 15,000.

10. Aqueous deodorizing composition for human and animal excrement consisting essentially of:
- tap water;
- an acid agent in an amount sufficient to neutralize ammonia and indolic amines in said excrement and reduce excrement pH to 4.6; and
- at least 0.1% up to about 10% of at least one biologically degradable, non-toxic and ecologically safe, water soluble polymer for forming, upon drying, a thin film vapor barrier on the excrement;
- wherein the acid agent includes a biodegradable carboxylic acid; and
- wherein the biologically degradable and water soluble polymer is a polymer selected from the group consisting of hydroxyethyl cellulose, polyethylene oxide, polyvinyl pyrrolidone, polyhydroxyethyl (meth) acrylate, polyvinyl alcohol, and polyhydroxypropyl methacrylate; and wherein the biologically degradable water soluble polymer has a molecular weight of higher than 15,000.

11. Deodorizing composition according to claim 1, wherein said water soluble film forming polymer has a molecular weight of about 16,000.

12. Deodorizing composition according to claim 9, further comprising Limonene.

13. Deodorizing composition according to claim 1 wherein said polymer comprises polyvinyl alcohol or polyvinyl pyrrolidone, and
said polymer is present in an amount of at least 1.5%.

14. The aqueous deodorizing composition of claim 13, wherein said acid is citric acid.

15. The deodorizing composition of claim 1 wherein the polymer is present in an amount of at least 2.5%.

16. The aqueous deodorizing composition of claim 9 wherein the biologically degradable and water soluble polymer has a molecular weight of about 16,000.

17. The aqueous deodorizing composition of claim 10 wherein the biologically degradable and water soluble polymer has a molecular weight of about 16,000.

* * * * *